United States Patent
Stutz et al.

(10) Patent No.: US 9,382,198 B2
(45) Date of Patent: Jul. 5, 2016

(54) PREPARATION OF LIGHT-COLORED ISOCYANATES

(75) Inventors: Herbert Stutz, Dormagen (DE); Reinhard Halpaap, Odenthal (DE); Tilak Suren Lewkebandara, Webster, TX (US)

(73) Assignees: Covestro Deutschland AG, Leverkusen (DE); Covestro LLC, Pittsburgh, PA (US)

( * ) Notice: Subject to any disclaimer, the term of this patent is extended or adjusted under 35 U.S.C. 154(b) by 1156 days.

(21) Appl. No.: 12/291,774

(22) Filed: Nov. 12, 2008

(65) Prior Publication Data

US 2009/0149671 A1 Jun. 11, 2009

Related U.S. Application Data

(60) Provisional application No. 61/003,000, filed on Nov. 14, 2007.

(51) Int. Cl.
*C07C 263/10* (2006.01)

(52) U.S. Cl.
CPC ..................................... *C07C 263/10* (2013.01)

(58) Field of Classification Search
None
See application file for complete search history.

(56) References Cited

U.S. PATENT DOCUMENTS

| | | | |
|---|---|---|---|
| 3,193,472 A | 7/1965 | Isacks, Jr. | |
| 3,859,323 A | 1/1975 | Bailey et al. | |
| 4,847,408 A | 7/1989 | Frosch et al. | |
| 5,286,760 A * | 2/1994 | Bolton et al. | 521/160 |
| 5,484,819 A | 1/1996 | Bolton et al. | |
| 5,872,278 A | 2/1999 | Kraus et al. | |
| 5,942,151 A | 8/1999 | Adkins et al. | |
| 6,248,926 B1 * | 6/2001 | Ostermaier et al. | 564/492 |
| 6,900,348 B1 | 5/2005 | Reif et al. | |
| 7,084,297 B2 | 8/2006 | Woelfert et al. | |
| 7,851,648 B2 | 12/2010 | Sohn et al. | |
| 2004/0024244 A1 * | 2/2004 | Walsdorff et al. | 560/347 |
| 2006/0116529 A1 | 6/2006 | Woelfert et al. | |
| 2006/0252960 A1 * | 11/2006 | Sohn et al. | 560/347 |
| 2007/0179316 A1 * | 8/2007 | Pohl et al. | 564/397 |
| 2007/0232827 A1 * | 10/2007 | Wolfert et al. | 560/347 |
| 2007/0287857 A1 | 12/2007 | Zechlin et al. | |
| 2008/0027242 A1 * | 1/2008 | Knosche et al. | 560/347 |

FOREIGN PATENT DOCUMENTS

| | | |
|---|---|---|
| CA | 2038126 A1 | 9/1991 |
| CA | 2606107 | 12/2013 |
| WO | WO 2005115974 | * 12/2005 |
| WO | WO 2005123665 | * 12/2005 |

* cited by examiner

*Primary Examiner* — Clinton Brooks
*Assistant Examiner* — Jennifer C Sawyer
(74) *Attorney, Agent, or Firm* — John E. Mrozinski, Jr.

(57) ABSTRACT

The invention relates to the preparation of isocyanates by phosgenation of amines in the gas phase, with these isocyanates having a comparatively low proportion of color-imparting compounds.

8 Claims, No Drawings

PREPARATION OF LIGHT-COLORED ISOCYANATES

CROSS REFERENCE AND RELATED APPLICATIONS

This application claims priority under 35 U.S.C. §119(e) to U.S. Provisional Application No. 61/003,000, filed Nov. 14, 2007, which is incorporated by reference into this specification.

FIELD OF THE INVENTION

The invention relates to the preparation of isocyanates by phosgenation of amines in the gas phase, with these isocyanates having a comparatively low proportion of color-imparting compounds.

BACKGROUND OF THE INVENTION

The phosgenation of aliphatic or aromatic amines for preparing isocyanates can be carried out particularly advantageously in the gas phase. Such processes have in principle been known for a long time in the prior art and have now become established in industry (EP-B 289 840).

A frequent problem is that, for whatever reason, these isocyanates are colored or undesirable secondary reactions occur in subsequent modification steps, for example prepolymerization, biuret formation or trimerization, and ultimately have an adverse effect on the color of the polyisocyanates obtained. The causes and sources of such discoloration are manifold since not all impurities present in the feed streams inevitably lead ultimately to undesirable discoloration in the direct process products or their downstream products.

SUMMARY OF THE INVENTION

It has now surprisingly been found that isocyanates which are obtained by phosgenation of amines have a light color or lead to particularly light-colored to uncolored polyisocyanates particularly when the parent amines which are used in the phosgenation have a PRI (polarographically reducible impurities) value of less than 60 mpm (moles per million moles).

DETAILED DESCRIPTION OF THE INVENTION

The present invention will now be described for purposes of illustration and not limitation.

The present invention therefore provides for the use of amines having a PRI value of less than 60 mpm in the preparation of isocyanates by means of phosgenation.

The invention further provides a process for preparing isocyanates by reacting the corresponding amines with phosgene in the presence or absence of an inert medium, wherein the amine stream fed to the phosgenation on average has a PRI value of less than 60 moles per million moles (mpm).

Preference is given to the amine stream having on average a PRI value of less than 40 mpm, particularly preferably less than 20 mpm, very particularly preferably less than 10 mpm.

The process of the invention is preferably carried out in a single stage. For the purposes of the present invention, this means that the mixing and reaction of the starting materials to form the product occurs in one reaction zone. After the products have left the reaction zone, preferably complete reaction of the amino groups introduced with phosgene has occurred. This is particularly worth striving for because otherwise unreacted amino groups can lead to hydrochloride or urea formation, which reduces the total yield of isocyanate and, owing to the formation of deposits, reduces the time for which the reactor can be operated.

Preference is likewise given to continuous operation of the process of the invention.

The PRI (polarographically reducible impurities) value of the amines is determined by reduction in aqueous solutions by differential pulse polarography (DPP) in the presence of zinc acetate as internal standard (−1.3 V vs. SCE) at −1.5 V vs. SCE at a static mercury drop electrode (SMDE) under a nitrogen atmosphere. The PRI values are calculated from the ratio of the peak heights and the concentration of the internal standard zinc.

Calculation of the amount of Zn (μmol) added as internal standard (in 10 ml of stock solution):

$$n(Zn) = \frac{m(Zn) \cdot 5 \text{ ml} \cdot 10 \text{ ml} \cdot F}{25 \text{ ml} \cdot 1000 \text{ ml} \cdot M(Zn)}$$

n(Zn) Amount (μmol) of zinc acetate added as internal standard m(Zn) Weight (g) of zinc acetate dihydrate used in the stock solution (dissolved in water to a volume of 25 ml and diluted 1:200 with water)

M(Zn) Molecular weight of zinc acetate dihydrate: 219.53 g/mol

F Conversion factor 106 μmol/mol

Calculation of the PRI value $$w(PRI) = \frac{n(Zn) \cdot M(\text{amine}) \cdot I(PRI) \cdot 100}{m(\text{amine}) \cdot w(\text{amine}) \cdot I(Zn)}$$

w(PRI): PRI content (mpm) of the amine sample
n(Zn) Amount (μmol) of zinc acetate added as internal standard
m(amine) Weight (g) of the amine to be examined used
M(amine) Molecular weight of the amine (in the case of hexamethylenediamine, 116.2 g/mol)
w(amine): Content (%) of amine in the sample analyzed
I(PRI) Current (nA) of the PRI peak
I(Zn) Current (nA) of the internal standard peak (Zn)

In the process of the invention, it is possible to use all amino-functional compounds having at least one primary amino group, preferably from 1 to 3 amino groups, as long as the amine stream fed into the reaction zone meets the abovementioned criterion in respect of the average PRI value. It is immaterial whether the amines are aliphatic, cycloaliphatic, araliphatic or aromatic.

Preferred amino-functional compounds usually have up to 18 carbon atoms and if a plurality of amino groups are present in the molecule, these are separated from one another by at least two carbon atoms.

Preference is given to using amines of the abovementioned type which can be brought into the gas phase without decomposition.

Particularly suitable amines for this purpose are diamines and triamines based on aliphatic or cycloaliphatic hydrocarbons having from 2 to 18 carbon atoms. Examples are 1,6-diaminohexane (hexamethylenediamine, HDA), 1-amino-3,3,5-trimethyl-5-aminomethylcyclohexane (IPDA) and 4,4'- and/or 2,4'-diaminodicyclohexylmethane. Preference is given to using 1,6-diaminohexane (HDA).

The process of the present invention can likewise be carried out using aromatic amines which can preferably be brought into the gas phase without decomposition. Examples of preferred aromatic amines are toluenediamine (TDA) as 2,4 or 2,6 isomer or a mixture thereof, diaminobenzene, 2,6-xylidine, naphthalenediamine (NDA) and 2,4'- or 4,4'-methylenedi(phenylamine) (MDA) or isomer mixtures thereof. Among these, preference is given to the diamines, particularly preferably 2,4- and/or 2,6-TDA.

The starting materials amine and phosgene can in each case also be fed together with an inert medium into the reaction space. The inert medium is a medium, which at the reaction temperature, is in gaseous form in the reaction space and does not react with the compounds made during the course of the reaction. The inert medium is generally mixed with amine and/or phosgene before the reaction, but can also be introduced separately from the feed streams. For example, nitrogen, noble gases such as helium or argon or aromatics such as chlorobenzene, dichlorobenzene, xylene, carbon monoxide or carbon dioxide can be used. Preference is given to using nitrogen and/or chlorobenzene as inert medium in the case of the amine, and in the case of phosgene, preference is given to using the hydrogen chloride obtained in the recovery of the phosgene which has been used in excess and/or carbon monoxide, nitrogen and/or chlorobenzene.

Preferably, the inert medium is used in such an amount that the ratio of gas volumes of the inert medium to gas volumes of amine or phosgene is from 0.001 to 5, preferably from 0.01 to 3, particularly preferably from 0.1 to 1. The inert medium is preferably introduced into the reaction space together with the amines.

The process of the invention is preferably carried out so that the starting materials amine and phosgene and also the isocyanate formed in the reaction zone are in the gaseous state under the reaction conditions, i.e. formation of liquid droplets is preferably ruled out.

Phosgene is used in a molar amount of from 1.0 to 10 based on the amine group, preferably from 1.2 to 4 based on the amine group.

To provide the abovementioned reaction conditions, the temperatures in the reaction zone are preferably greater than 200° C., particularly preferably greater than 260° C., very particularly preferably greater than 280° C. The upper temperature limit is preferably not more than 570° C., particularly preferably not more than 500° C.

The reaction of phosgene with amine in the respective reaction zone occurs at absolute pressures of from >0.1 bar to <20 bar, preferably from 0.5 bar to 10 bar, particularly preferably from 0.7 bar to 5 bar, very particularly preferably from 0.8 to 3 bar.

In general, the pressure in the feed lines into the reaction zone is higher than the pressure indicated above in the reaction zone itself. The pressure in the feed lines is preferably from 20 to 2000 mbar higher, particularly preferably from 30 to 1000 mbar higher, than in the reaction zone itself.

In general, the pressure in the regions of the process adjoining the actual reaction zone preferably is lower than in the reaction zone itself. The pressure there is preferably from 10 to 500 mbar lower, particularly preferably from 30 to 150 mbar lower, than in the reaction zone.

The starting materials are preferably introduced into and passed through the reaction zone at a flow velocity of in each case from 3 to 100 m/s, preferably from 10 to 50 m/s.

The flow velocities of the two starting materials are preferably set within the abovementioned ranges in such a way that an average contact time of the reaction mixture of amines and phosgene of generally from 0.01 seconds to less than 15 seconds, preferably from >0.04 seconds to <10 seconds, particularly preferably from >0.08 seconds to <5 seconds, is achieved in the reaction zone. For the present purposes, the average contact time is the period of time from the commencement of mixing of the starting materials until they leave the reaction space on their way to the work-up stage. In a preferred embodiment, the flow in the process of the invention is characterized by a Bodenstein number of greater than 10, preferably greater than 100 and particularly preferably greater than 250.

The dimensions of the reaction space and the flow velocities are advantageously selected so that turbulent flow, i.e. flow having a Reynolds number of at least 2300, preferably at least 2700, of the reaction mixture prevails, where the Reynolds number is formed using the hydraulic diameter of the reaction space.

As a result of the turbulent flow, a narrow residence time having a low standard deviation of less than 10%, preferably less than 6%, is achieved.

The reaction zone preferably has no movable internals.

The reaction zone can be heated/cooled via its external surface. To build production plants having high plant capacities, a plurality of reactor tubes can be connected in parallel. However, the reaction can also be carried out adiabatically. This means that heating or cooling energy does not flow by means of engineering measures through the external surface of the reaction volume. The reaction preferably takes place adiabatically.

After the reaction mixture has been reacted in the reaction zone, rapid cooling of the reaction gases after the phosgenation reaction to temperatures below 150° C. is necessary to avoid formation of undesirable by-products as a result of the thermal decomposition of monoisocyanate/diisocyanate/triisocyanate or as a result of further reaction by oligomerization/polymerization, as the isocyanates formed are not thermally stable for a prolonged period at the reaction temperatures of from 260 to 570° C. Cooling to temperatures of from 100 to 150° C. is carried out in a single-stage or multistage scrub (quench with scrubbing column) using an inert solvent, as described in EP-A1 1403248, col. 2, line 39-col. 3, line 18.

Suitable solvents are preferably hydrocarbons which may optionally be substituted by halogen atoms, for example chlorobenzene, dichlorobenzene and toluene. Particular preference is given to using monochlorobenzene as solvent. It is also possible to use the isocyanate or a solution of the isocyanate prepared, which can also be circulated via a heat exchanger to remove energy, as solvent. In the scrub, the isocyanate is transferred selectively to the scrubbing solution. The solvent is recovered from the remaining isocyanate-free gas (excess phosgene, hydrogen chloride, any inert medium and solvent from the scrub) by partial condensation and the phosgene is subsequently recovered, e.g. by means of absorption in monochlorobenzene, and the hydrogen chloride is purified as described in the prior art and reused as raw material. The concentrated isocyanate solution obtained in the quench and scrubbing column is preferably freed of physically bound (dissolved) and chemically bound hydrogen chloride and phosgene by means of rectification and separated into solvent, low-boiling by-products, isocyanate and high boilers in further distillation steps. Preference is given to using the isocyanate.

The diisocyanates and/or triisocyanates which can be obtained in this way can be used particularly advantageously in the production of polyurethane coatings and also adhesives and sealants. For this purpose, they are preferably firstly reacted to form oligomeric polyisocyanates, e.g. isocyanurates, iminooxadiazinediones, biurets, uretdiones, allophanates and/or prepolymers, and also, if appropriate, blocked by methods known in industry.

The diisocyanates and/or triisocyanates which can be obtained by adhering to the inventive PRI values in the amine stream lead in the case of aliphatic polyisocyanates to Hazen color numbers of ≤150 APHA, preferably ≤100 APHA.

EXAMPLES

The present invention is further illustrated, but is not to be limited, by the following examples.

The determination of the hydrolyzable chlorine content (HC value) was carried out by potentiometric titration: the sample to be analyzed was admixed with methanol and refluxed for 10 minutes to form urethane. The mixture obtained was subsequently diluted with water and hydrolyzed by boiling under reflux. The ionogenic chlorine formed here was, after acidification with nitric acid and addition of a known mass of sodium chloride, titrated argentometrically with a standard silver nitrate solution. The titration was carried out drift-controlled (equilibrium titration) with incremental introduction of reagent and automatic equivalence point detection.

Example 1

In a tube reactor provided with downstream isocyanate condensation stage and subsequent isocyanate work-up, hexamethylene diisocyanate was prepared continuously from the starting materials hexamethylenediamine and phosgene by reaction in the gas phase. The temperatures of the two feed streams were 300° C. The pressure in the tube reactor was slightly above atmospheric pressure at 1400 mbar. Phosgene was used in an excess of 100 mol % of theory. As a result of the adiabatic reaction conditions, the temperature in the reactor rose to about 450° C.

The hexamethylenediamine fed into the reaction had a PRI content of less than 10 mpm (moles per million moles).

The reaction product hexamethylene diisocyanate (HDI) was, after leaving the reactor, condensed, separated from the by-product hydrogen chloride, the inerts and the excess phosgene and subsequently purified in the distillation sequence. The HDI obtained had a content of hydrolyzable chlorine of 15 ppm.

The HDI obtained in this way was processed further (in a manner analogous to Example 2 of EP 1158013 A1, p. 5) to form a biuret, a trifunctional polyisocyanate having a very low vapor pressure which is employed in surface coating systems. The biuret is virtually clear and colorless with a Hazen color number of 30 APHA.

Example 2

Comparative Example

Example 1 was repeated under the same reaction conditions.

The hexamethylenediamine fed into the reaction had a PRI content in the range from 60 to 80 mpm (moles per million moles); the average was 75 mpm.

The HDI obtained from the distillation sequence had a content of hydrolyzable chlorine of 40 ppm.

The HDI obtained in this way was further processed as in Example 1 to form a biuret, a trifunctional polyisocyanate having a very low vapor pressure which is employed in surface coating systems. The biuret has a light yellowish color and a Hazen color number of 80 APHA.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for preparing an isocyanate by reacting an amine with phosgene in the presence or absence of an inert medium, the improvement comprising an amine stream fed to the phosgenation on average having a PRI value of less than 60 moles per million moles (mpm), wherein the phosgenation of the amine is performed so that formation of liquid droplets in the reaction zone does not occur, and wherein the phosgenation is carried out in the gas phase.

2. The process according to claim 1, wherein the amine stream has a PRI value of less than 10 mpm.

3. The process according to claim 1, wherein the amine is selected from the group consisting of aliphatic, cycloaliphatic or aromatic amines.

4. The process according to claim 1, wherein the phosgene stream fed into the reaction zone has an HCl content of from 0.1 to 10% by weight.

5. The process according to claim 1, wherein the inert medium is selected from the group consisting of nitrogen, carbon monoxide, chlorobenzene and mixtures thereof.

6. The process according to claim 1, wherein reaction in a reaction zone is carried out at above 200° C. but not more than 570° C. and absolute pressures of from 0.8 to 3 bar, with pressure in the amine or phosgene feed lines being from 20 to 2000 mbar above pressure in the reaction zone and pressure in the zones downstream of the reaction zone being from 10 to 500 mbar below pressure in the reaction zone.

7. The process according to claim 1, wherein the amine and phosgene are fed into and passed through a reaction zone at a flow velocity of in each case from 3 to 100 m/s and the mean contact time of the reaction mixture of amines and phosgene is from 0.01 seconds to less than 15 seconds.

8. The process according to claim 1, wherein the process is operated adiabatically.

* * * * *